United States Patent [19]
Rupp et al.

[11] Patent Number: 5,661,249
[45] Date of Patent: Aug. 26, 1997

[54] APPARATUS AND METHOD FOR INSPECTING SMALL ARTICLES

[75] Inventors: Michael Rupp, Pforzheim; Werner Schiffer, München; Gyula Varhaniovsky, Pfinztal; Thomas Kirchner, Karlsruhe; Nikolaus Asteriadis, Baltmannsweiler, all of Germany

[73] Assignee: Walter Grassle GmbH, Pfinztal-Sollingen, Germany

[21] Appl. No.: 513,621

[22] Filed: Aug. 10, 1995

[30] Foreign Application Priority Data

Aug. 11, 1994 [DE] Germany .................. 44 28 452.7
Mar. 31, 1995 [DE] Germany ................. 195 11 854.5

[51] Int. Cl.⁶ .................................................. G01N 15/02
[52] U.S. Cl. .............................. 73/865.8; 73/863; 73/45
[58] Field of Search ........................ 73/863.45, 863.92, 73/864, 864.62, 865.8

[56] References Cited

U.S. PATENT DOCUMENTS

| | | | |
|---|---|---|---|
| 3,757,943 | 9/1973 | Chae et al. | 209/111.7 |
| 3,920,541 | 11/1975 | VandenBerg et al. | 209/74 R |
| 4,318,081 | 3/1982 | Yoshida | 340/146.3 H |
| 4,593,190 | 6/1986 | Kawasaki et al. | 250/233 R |
| 4,980,292 | 12/1990 | Elbert et al. | 435/289 |
| 5,157,976 | 10/1992 | Tokoyama et al. | 73/865.8 |
| 5,515,740 | 5/1996 | Gamberini | 73/865.8 |

FOREIGN PATENT DOCUMENTS

| | | |
|---|---|---|
| 2617457 | 4/1976 | Germany . |
| 2659461 | 12/1976 | Germany . |
| 2818876 | 4/1978 | Germany . |
| 3608398 | 3/1986 | Germany . |
| 4032327 | 10/1990 | Germany . |
| 4123916 | 7/1991 | Germany . |
| 4139189 | 11/1991 | Germany . |
| 4202172 | 1/1992 | Germany . |

*Primary Examiner*—George M. Dombroske
*Assistant Examiner*—Max H. Noori
*Attorney, Agent, or Firm*—Antonelli, Terry, Stout & Kraus, LLP.

[57] ABSTRACT

The invention is a method and an apparatus for inspecting small articles. The invention includes a first rotatable support having a first circumferential surface for holding the small articles; a second rotatable support having a second circumferential surface with the first and second circumferential surfaces being opposed to each other and spaced apart at a closest separation which is greater than a thickness of the small articles and is a transfer point for transferring the small articles from the first circumferential surface to the second circumferential surface; a vacuum source coupled to suction holes disposed at spaced apart locations on the first circumferential surface for holding the small articles at the spaced apart locations during rotation to the transfer point; a vacuum source coupled to suction holes disposed at spaced apart locations on the second circumferential surface for holding the small articles at the spaced apart location during rotation from the transfer point; and a plurality of detector devices, one of the detector devices being offset radially outward from and facing the second circumferential surface of the second rotatable support for viewing one of a top or bottom surface of the small articles and at least another of the plurality of detector devices being positioned for viewing at least one other surface of the small articles.

27 Claims, 4 Drawing Sheets

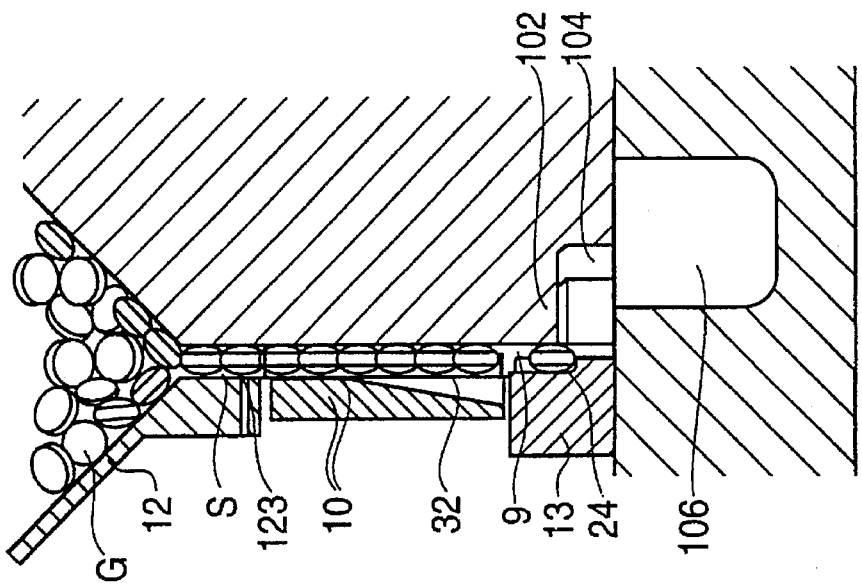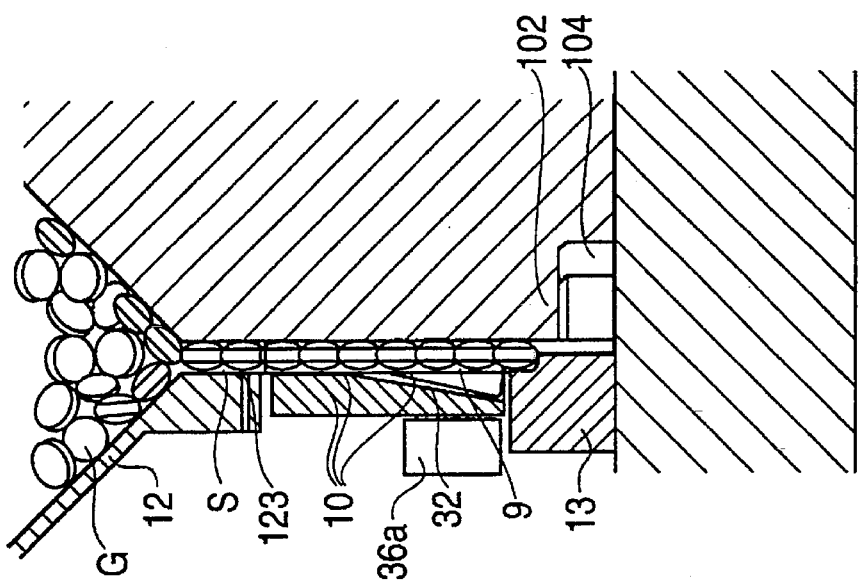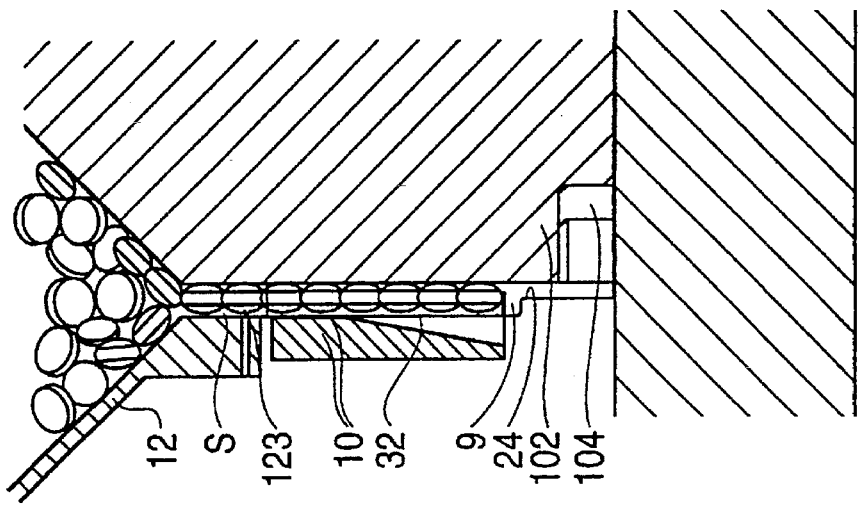

APPARATUS AND METHOD FOR INSPECTING SMALL ARTICLES

BACKGROUND OF THE INVENTION

1. Field of the Invention

The invention relates to an apparatus and method for inspecting small articles, such as in particular tablets, film tablets, dragees, capsules, etc., the articles being held for inspection purposes by means of vacuum on supports rotating about axes.

2. Description of the Prior Art

Tablets, etc. must to an increasing extent be inspected for defects. If a precisely defined tablet treatment dose is predetermined, this dose would be modified if a patient should ingest a tablet with a break. In the case of film tablets and dragees, the active ingredients contained therein must be supplied in delayed form to the body and for this purpose the tablets and dragees are provided with a coating. If the coating is damaged or at least in part absent, then there is a change to the characteristics and/or action of the ingested medicament. This must be avoided and can be prevented if the tablets, film tablets, dragees, capsules, etc. are inspected for lack of damage and completeness. It is necessary to check their entire surface. This can take place by means of an apparatus for inspecting such articles.

In addition, it must be ensured in the case of such an apparatus that during the inspection of the articles such as tablets and the like no residues of the tested articles are left behind on the conveying members, even in very small amounts, e.g. in the form of dust. Thus, if the same conveying members were then used for other products such as tablets, etc., the residues left behind by the previously inspected products, such as e.g. in dust form, could adhere to the subsequently inspected products, which must be completely avoided. To prevent this all the product-contacted parts of the apparatus must be cleaned. However, this takes a considerable time and can lead to undesired stoppage times on the part of the inspection apparatus.

German patent 42 02 172 discloses an apparatus of the aforementioned type, in which the articles to be tested are supplied to receptacles of at least one first, rotary disk. They can optionally be held with suction force in the receptacles. There is no precise supply to the receptacles. Following the inspection of the top of the articles they are transferred to a second disk located above and running synchronously to the first, rotary disk, where the articles hang on suction holes, so that their underside can be inspected. As a function of the inspection result the articles are removed from the second disk and sorted. The delivery from the first to the second disk takes place by raising the articles on the first disk until they are in the immediate holding range of the second disk. As a result, for at least a short time, the articles are subject to an influence disturbing the positioning through centrifugal force. Thus, either the speeds of the disks must be reduced, so that there is an output limitation, or no precise positioning is possible. An imprecise positioning can lead both on the first and second disks to articles such as e.g. spherical tablets assuming an inclined position relative to the detection direction, which leads to optically distorted images. Moreover, when using video cameras the image detail must be enlarged, which requires a higher calculating power for evaluation and therefore leads to an output limitation and/or a poorer resolution and correspondingly inferior inspection results. The inclined positions are also problematical with respect to a reflection-free illumination. Because the centrifugal forces act at right angles to the holding forces, the effective holding force only corresponds to the frictional force, which is produced by the holding force. This also leads to a significant speed reduction. The undefined supply of the articles to the first disk is also disadvantageous. As a result of the undefined residence time and very high relative speeds between the articles and the first disk, the articles to be tested can even be damaged. The use of movable mechanical components, such as e.g. a ram leads to considerable problems when cleaning the apparatus. The application of a vacuum by the suction channels, e.g. in the transfer area from the first to the second disk, requires the most careful cleaning of the ram and the suction channels, in order to avoid cross-contaminations.

According to German patent 36 08 398 articles are conveyed by a conveying mechanism, which essentially comprises two driven, endless belts, which are guided over pulleys with an adjustable reciprocal spacing and are received in stationary plates. The articles are subject to suction action via the spacing or gap and are in this way held on the belts. Such a first conveying mechanism on which the articles are located is followed by a second mechanism on which they are suspended. The articles are visually observed by means of several line cameras. For observing the lateral faces the two conveyor belts of a conveying mechanism have a relative speed with respect to one another. In this way the articles are then rotated about their vertical axis. According to this document, the articles are separated on a rotary table with guiding devices and sorting gates.

In the case of line cameras the resolution and therefore the detection precision is dependent on the conveying speed of the articles to be inspected. Apart from possible operating errors this also suffers from the disadvantage that the throughput is inversely proportional to the dimensions of the articles to be inspected, i.e. the throughput decreases with increasing length of the articles in the conveying direction. As a result of the in part concealed gaps in the conveying system, the cleaning of the apparatus is also extremely time-consuming. As a result of the rotation of the articles by the conveying mechanism it is only possible to a limited extent to observe their lateral faces. The rotation of the articles by the relative movement of the conveyor belts even in the case of substantially round articles such as tablets can lead to inclined positions and therefore to distortions and/or light reflections and is not even possible with oblong tablets. The sought after complete surface check is then not possible or is only possible with limitations. The nature of the separation in the case of this apparatus also involves high cleaning costs and a high damage risk for the articles.

SUMMARY OF THE INVENTION

The objective of the invention is therefore to provide an apparatus and a method for inspecting small articles such as in particular tablets, film tablets, dragees, capsules, etc., the apparatus being easily cleanable with a limited risk of cross-contamination and in which at high speeds it is possible to work with relatively low suction pressures.

According to the invention the problems of the prior art are solved by an apparatus for inspecting small articles of the aforementioned type having the articles sucked by vacuum against a substantially coaxially arranged circumferential surfaces of a support. A method according to the invention is characterized in that the articles are subject to vacuum action and are supplied in a precisely defined position in the substantially coaxially arranged circumferential surfaces of a first support. Preferably the articles are sucked by means of a vacuum into radial suction holes, distributed over the circumferential surface and located on the circumferential surface of the support. Therefore the articles are held at precisely defined positions of the circumferential wall of the support and can be inspected for defects by means of suitable detection devices. Due to the fact that the articles are held in precisely defined suction holes on the support, they can also be delivered in a precisely defined position, so that an inspected article such as a tablet, dragee, film tablet, capsule, etc. and the test result associated therewith always remain associatable with one another. A support can easily be fixed by means of screw connections to its drive, so that it can be easily replaced. Thus, if after the inspection of one type of articles it is necessary to inspect a different type of article, it is merely necessary to replace the support, which can take place rapidly. The previously used support can then be cleaned, without holding up for a long period the further use of the apparatus and thereby causing long idle times. In order to also be able to clean the suction holes on the supports following each revolution of the particles adhering thereon, preferably the suction holes or bores of the support are subject to compressed air action at least once in opposition to the suction direction after each revolution.

Due to the fact that the articles are held on circumferential walls of the support, the exerted vacuum acts opposite to the centrifugal forces acting on the articles, so that the amount of the suction force must merely overcome this.

According to a further development of the invention a device is provided for supplying the articles to a first support. Preferably, the articles undergo separation or individualization prior to positioning on the circumferential surface of the first support. This can take place by a separating mechanism with a fixed, downwardly tapering hopper for supplying the articles, the hopper having a bottom-connected cylindrical attachment, which forms with a rotary insert fixed to the support and arranged in concentric, synchronous manner to the support an annular gap, which has a slightly larger thickness than that of the articles to be inspected. The rotary insert constructed as a separating section is preferably provided in the lower area with webs or ribs fixed between grooves or shafts, the grooves or shafts having a width slightly exceeding the width of the articles. In such shafts initially several articles can be intermediately stored, which ensures that at the outer end of such a shaft there is an article for delivery to the support and there is no idling of the apparatus. The hopper offers a possibility for a high article throughput and as a result of the cylindrically constructed attachment the articles to be separated drop into the annular gap vertically solely under the influence of gravity without any action thereon of transverse forces, which could also cause damage. This prevents crushing and also accumulations.

By means of unlockable retaining members for closing the grooves or shafts in the downwards direction it is ensured that the articles do not pass in uncontrolled manner into the area upstream of the suction holes. The retaining members are preferably lamellar springs, which can be unlocked by magnets. By means of a bypass provided in preferred manner and equipped with a support curve the articles are supplied in a positionally accurate manner to the suction hole of the first support after unlocking the lamellar springs.

The inspection of the articles retained in the suction holes takes place by means of a detector device arranged radially to a first support and whose movement path faces the suction holes holding the articles on the support.

In order to be able to inspect the entire surface of the articles, the invention provides a further support with suction holes located on a circular path in a circumferential wall, the circumferential walls of the support moving past one another synchronously, but in opposition with a spacing somewhat exceeding the thickness of the articles, the suction holes face one another and at a transfer point, at which the circumferential surfaces of the two supports are oriented parallel to one another, are in alignment with one another. In order to assist the transfer of the articles from one support to another or the positioning on the first support, the suction holes of the supports are connectable to stationary suction channels. In the first support the suction hole is connected to the associated, stationary suction channel for producing the vacuum only following the positioning of the articles. The transfer of the articles from one support to the other takes place in the case of simultaneous assistance by means of centrifugal force in that the suction holes of the first support leave the area of the associated stationary suction channel, i.e. the suction action is eliminated, whereas the suction holes of the second support reach the area of the associated suction channel, so that there is a suction action in the direction of the second support. The articles are sucked by one area onto the suction holes of the further support and it precisely faces the area with which they are directed to the suction holes of the first support, so that same is now exposed and can also be optically inspected.

According to a preferred development this takes place in that detection devices are provided in the vicinity of the movement path of the suction holes and one of them is oriented radially to the support and faces the latter, whereas at least one further device is axially parallel and faces the movement path of the suction holes. This makes it possible to also optically inspect the lateral faces of the articles. The detector devices are preferably camera systems with in each case have a casing, a lighting device and a camera, particularly a video camera. For inspecting the lateral faces of the articles at least one camera system has correspondingly arranged mirrors.

The illuminating devices preferably illuminating the articles by means of diffuse light can in each case have several light emitting diodes of different wavelengths. In this way it is possible to separately control in a groupwise manner light emitting diodes of the same wavelength and therefore choose the light wavelength suitable for the article to be inspected. To create an adequately sharp contrast between the articles to be inspected and the support, the latter preferably has a contrasting colour to the article to be inspected. It is also possible for the lighting devices to in each case have a light emitting diode and then the lighting devices can be simply replaced as a complete unit.

In order to keep the air space between the video camera lens and the articles free from dust, the casing under gas pressure by means of filtered air preferably has air exit openings in the direction of the suction holes.

The video images received by the video cameras are then transferred to a selection unit for defect detection purposes. Divergences from the geometrical shape, e.g. through larger breaks, can easily be detected. To be able to detect smaller surface defects, there is generally a nominal-actual value comparison between produced and stored images. As the articles to be inspected can have notches or embossings, so that a positionally accurate separation of the articles is prevented, a nominal-actual value comparison involve a mathematical rotation of the produced video images. This would significantly increase the calculating expenditure required and therefore also the time required. Thus, preferably an evaluation takes place, which evaluates the gradients of the grey value change of adjacent image points.

Production-caused irregularities of the surface, such as notches or embossings, have relatively shallow gradients and regular paths, whereas faults have steep gradients and/or irregular paths. This allows a reliable inspection of the articles with a good resolution in the millisecond range.

For the delivery of the articles ejection devices are provided for the articles detected as being poor or satisfactory. The articles are delivered by ejection devices, which preferably have blast nozzles.

The articles found to be defective and the articles found to be satisfactory are in each case ejected by means of different ejecting devices. Articles left behind on the second support are classified as defective and are ejected as such. Thus, a further processing of faulty articles is prevented in an optimum manner.

The invention provides an apparatus enabling tablets, dragees, film tablets, capsules, etc. to be inspected with a throughput of several thousand articles per minute in such a way that the entire surface can be inspected for freedom from defects. Idle times are reduced, because the articles only come into contact with those parts which can be easily replaced, so that the time needed for cleaning these does not lead to apparatus stoppage times. The inspection is validatable as a whole.

BRIEF DESCRIPTION OF THE DRAWINGS

Further advantages and features of the invention can be gathered from the following description of a preferred embodiment of the invention with reference to the attached drawings:

FIG. 3 is a section through the separating area of the apparatus prior to separation.

FIG. 4 is a section through the separating area during separation.

FIG. 5 is a section through the separating area after separation.

DETAILED DESCRIPTION OF THE PREFERRED EMBODIMENT

Figure 1:
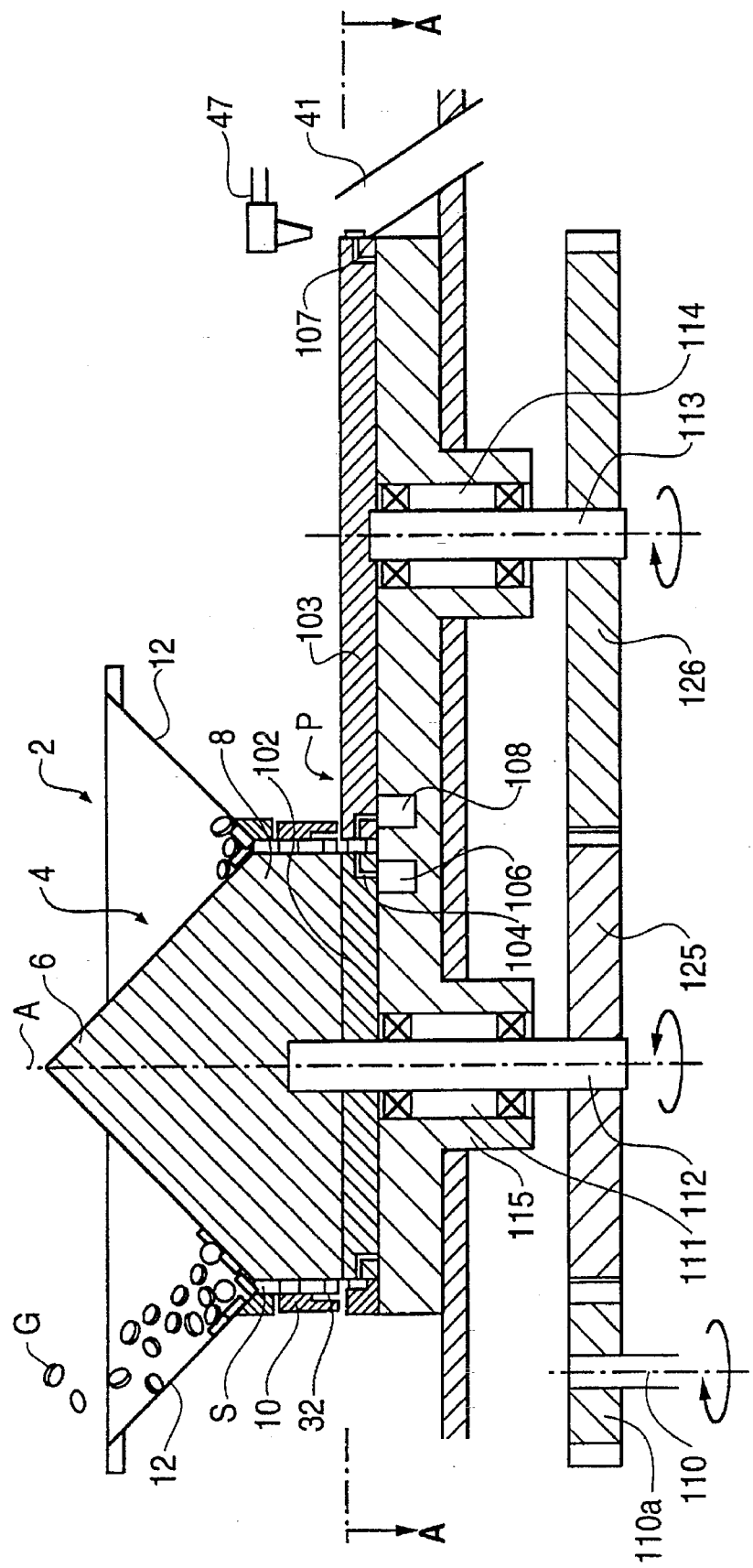
FIG. 1 is a diagrammatic vertical section through a preferred embodiment of the inspection apparatus according to the invention corresponding to B—B in FIG. 2.

The apparatus according to the invention shown in FIG. 1 has a separating device 2 for the articles G to be inspected, such as tablets or the like, as well as a testing or inspecting device P. The separating device 2 has a rotationally symmetrical separating body 4, which is rotatable about its axis of symmetry A and is rotated when the apparatus is operating. The separating body 4 has an upper, substantially conical feed section 6, to which is connected a substantially cylindrical separating section 8, which forms magazines to be described hereinafter.

In particular in the vicinity of its feed section 6, the separating body 4 is surrounded by a torus 12 in the form of a hopper. As from the transition area from the feed section 6 to the separating area 8 between the latter and the lower area of the torus 12 is formed a ring slot S, which has a slightly greater thickness than that of the articles G to be tested.

Figure 6:
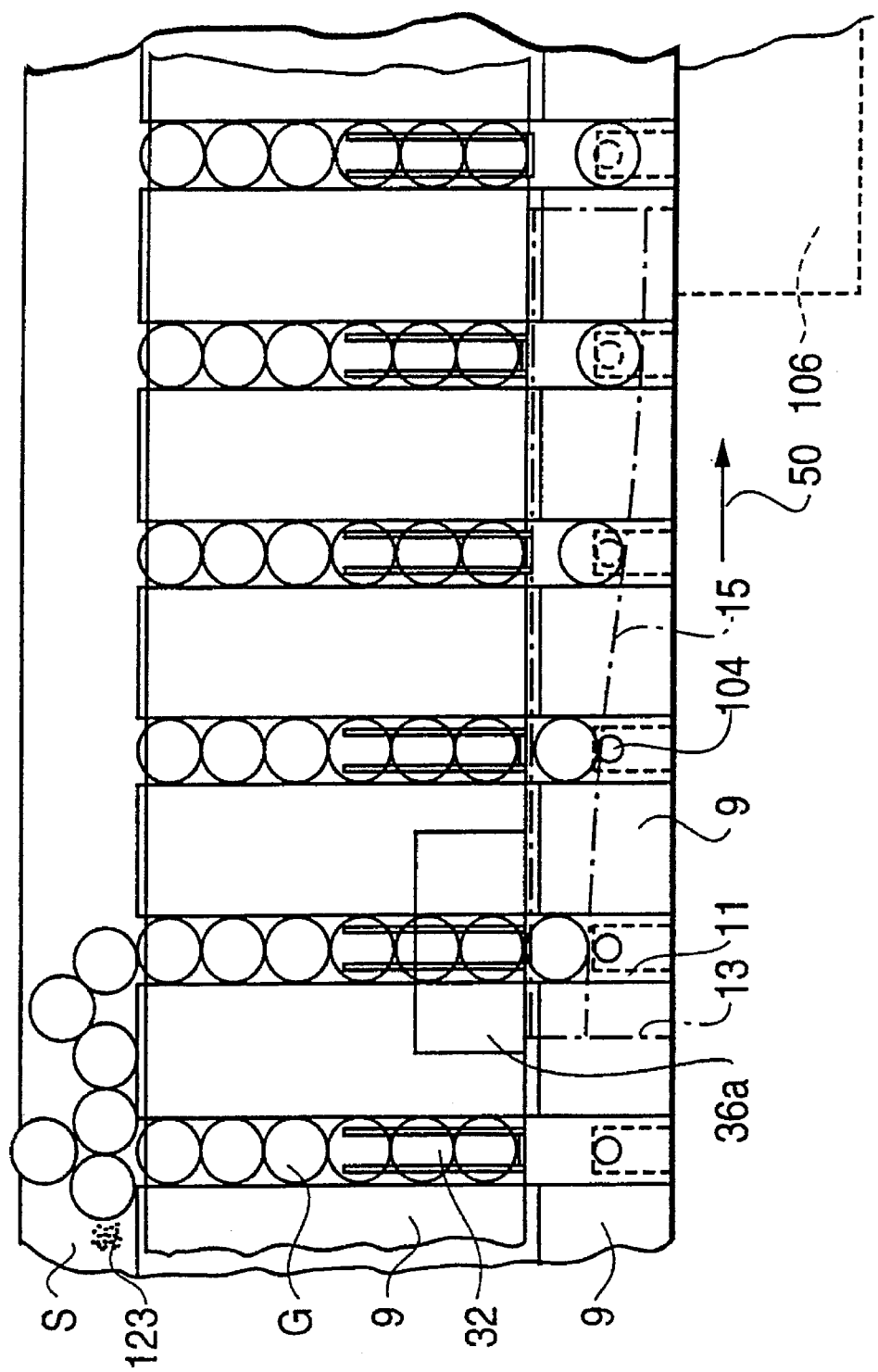
FIG. 6 is a development of the support in the separation area.

At the separating section 8 in a lower area below the ring slot S FIG. 6) webs or ribs 9 are formed, between which are formed grooves or shafts 11, whose width slightly exceeds the width of the articles G or the diameter thereof. The bottom of the grooves or shafts 11 is aligned with the face of the cylindrical separating section 8 in the vicinity of the slot S. In the radial direction the grooves or shafts 11 are closed by a circular cover 10 firmly connected to the separating body 4 or its separating section 8. In the upwards direction towards the ring slot S, the grooves or shafts 11 are open, whereas in the downwards direction they are closed by lamellar springs 32. The cover 10 ends in the lower area at the same height as the springs 32. Below the springs 32 the radial height of the webs 11 is reduced to approximately half the thickness of the articles G. In the lower area the separating body 4 and in particular its separating section 8 is constructed as a support 102 for the articles G or is firmly connected to such a support 102.

Over a partial circumference of the support 102 are provided stationary magnets 36a, which act in contactless manner on the lamellar springs 32 moved past and which have on their underside a horizontal bend and consequently raise them to such an extent that the grooves or shafts 11 are freed at the bottom and an article G can slide through downwards. The springs 32 are supported on the cover 10.

In the same area as the magnets 36a a bypass means 30 is provided in a stationary manner and has a support curve 15, which extends radially roughly up to half the thickness of the articles G. When the spring 32 is open the curve 15 allows an article G to slide in the groove initially to completely below the spring 32. The curve 15 is lowered to such an extent that a separated article G comes to rest concentrically or centrally in front of a suction hole 104.

The support 102 for the articles G together with the separating body 4 is located on a shaft 112, which is mounted in a pivot bearing 111 in a stationary machine part 115. The shaft 112 is also connected in non-rotary manner to a toothed disk 125, which has the same diameter as the support 102 and is driven by means of a pinion 110a connected to a driving shaft 110 by a not shown drive.

In the stationary machine part 115 a suction channel 106 is formed over a partial circumference. In the outer circumferential wall of the support 102 are formed suction holes 104, which can be brought by means of a suction channel into fluid connection with the suction channel 106 in the stationary machine part 115.

Alongside the support 102 is provided a second support 103 in the form of a circular disk, which also has in its circumferential walls suction holes 107, which are connected by means of suction channels to a suction channel 108 in the stationary machine part 115. The support 103 by means of a shaft 113, which is mounted by means of a bearing 114 in the stationary machine part 115, can be driven by a toothed disk 126, whose diameter corresponds to the support 103 and which meshes with the toothed disk 125. The channels 106 and 108 are connected to at least one vacuum pump (not illustrated).

As a result of the synchronous drive of both supports 102, 103 by means of the meshing toothed disks 125 and 126 with opposite rotation direction connected to the shafts 112 and 113 the supports 102 and 103 in a transfer point 105 have the same circumferential speed and the same movement direction. The supports 102 and 103 are so connected by the shafts 112 and 113 that the suction holes 104 and 107 at the transfer point 105 are guided in a precisely aligned manner, so that there the articles G to be tested can be transferred without any relative position change from one support 102 to the other support 103. For transfer purposes the suction holes 104 in the transfer area 105 leave the area of the stationary suction channel 106, so that the suction action for the support 102 is eliminated. At the transfer point 105 the suction holes 107 reach the area of the stationary suction channel 108, so that as from this transfer point 105 the suction action for the support channel 103 is produced.

Figure 2:
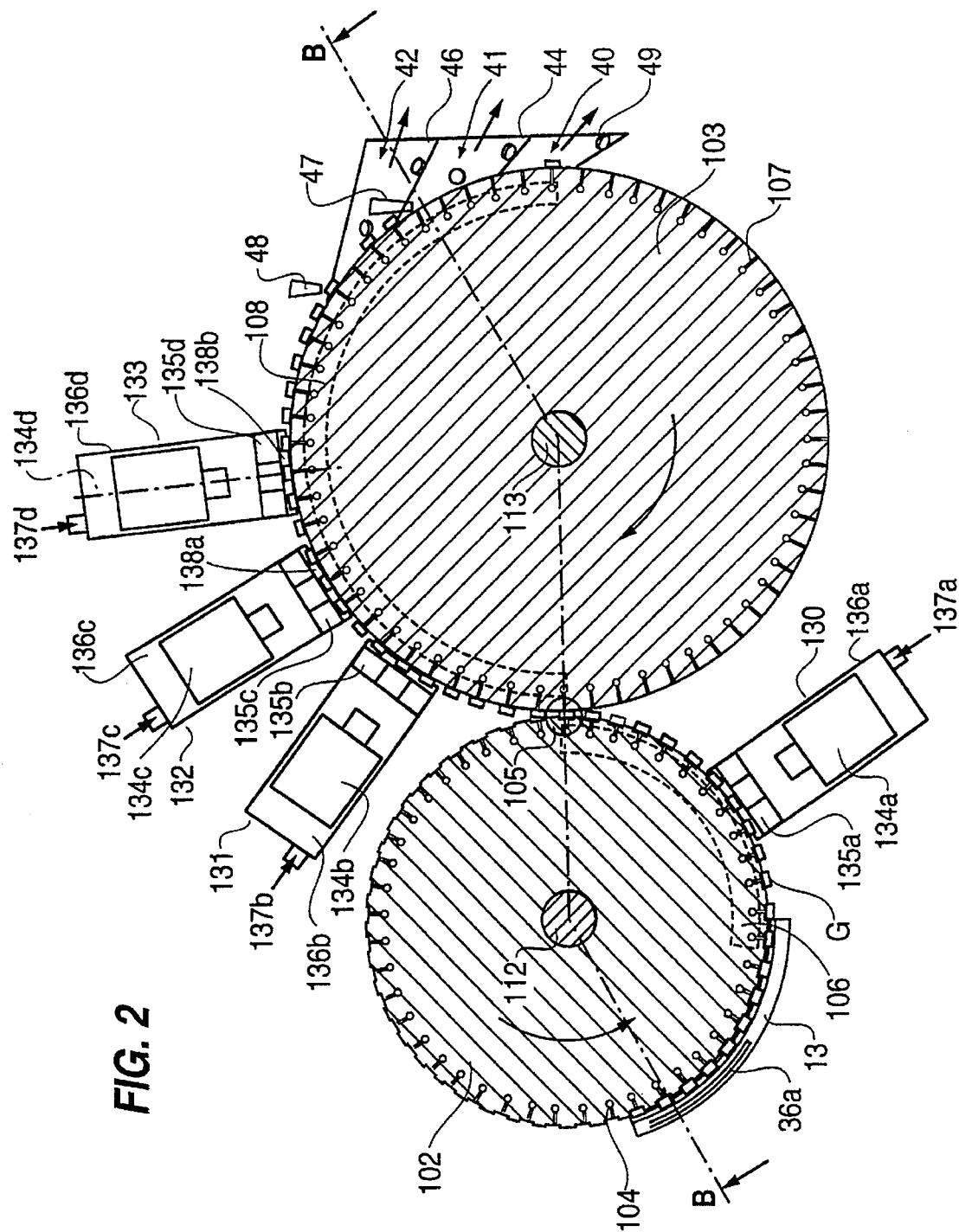
FIG. 2 is a diagrammatic cross-section through the testing apparatus corresponding to A—A in FIG. 1.

Alongside the support 102 is provided a stationary camera system 130. Camera systems 131, 132 and 133 are positioned on the circumference of the support 103. The camera systems 131–133 can be positioned alongside, above and below the path traversed by the suction holes 107 of the support 103 (FIG. 2). The camera systems 130–133 are connected to image processing units (not illustrated) The camera systems 130–133 respectively have a casing 136a–d respectively with lighting devices 135a–d and cameras 134a–d, in particular a video surface camera. In the represented embodiment, the camera systems, 132 and 133 are also provided with mirrors 138a and b for observing the circumferential faces of the articles G.

In order to avoid any impairing of the image quality and a faulty testing or inspection of the articles due to the entry of dust into the air space between the lens of the cameras 134a–d and the articles and consequently to keep the air space free from dust, filtered air is supplied to the casings 136a–d so that filtered air can pass out of the casings in the direction of the articles G.

The lighting devices 135a–d can be equipped with a plurality of light emitting diodes having different wavelengths and diodes having the same wavelength can be separately controlled in groupwise manner. However, it is also possible to provide the lighting devices 135a–d with only light emitting diodes of the same wavelength, so that the lighting devices 135a–d can be simply replaced as a complete unit for illumination with a different wavelength.

The camera systems 136a–d used for the optical testing and inspection processes are connected by means of connections 137a–d to an image evaluation unit (not illustrated) by means of which the images or pictures taken by the camera 134a–d can be evaluated. The image evaluation unit is designed in such a way that there is an evaluation of the gradients of the grey value change of adjacent image points. This makes it possible to detect breaks, varnish damage, as well as displacements, particularly in the case of multicoating tablets, and in particular the smallest surface defects, so that the articles suffering from these problems can be eliminated.

For this purpose below the support 103 in the circumferential direction behind the camera systems 131–133 are provided ejection devices 40, 41, 42 in the form of ejection chutes. The ejection devices 41 and 42 have continuation channels 44 and 46 for the articles G, as well as ejection devices in the form of blast nozzles 47, 48 with which the articles G can be separated from the support 103 by an air jet, so that they drop into one of the continuation channels 44, 46. Thus, the blast nozzle 48 ejects the defective articles G into the channel 46, whereas the blast nozzle 47 ejects the satisfactory articles G into the continuation channel 44. The ejection device 40 is only provided with a continuation channel 9. As the suction channel 108 terminates at the start of the continuation channel 49, all articles not ejected for some reason by one of the ejecting devices 47, 48 as a result of the elimination of the vacuum at the suction holes 107, automatically drop into the continuation channel 49 and are disposed of as defective articles. As a result of this measure it is very reliably ensured that only satisfactory articles G pass into the channel 44 and are further processed.

Objects or articles G to be inspected, such as tablets, dragees, film tablets, capsules, etc., are first supplied by means of a supply mechanism not illustrated, to the separating device 2. The articles G to be inspected drop via the supply device into the central area of the conical feed section 6 and slide on the cone up to the inlet of the ring slot S and are oriented by the rotary movement in such a way that they rest flat on the conical feed section 6, i.e. with their height perpendicular to the face of the conical section 6, so that they can in this way slide with a horizontally oriented height into the ring slot S. In addition, a member is provided for breaking up an accumulation of the articles arriving at the slot S and in the represented embodiment it is constituted by a brush 123.

In the ring slot S the articles G accumulate in the oriented manner and are individually received by the grooves or shafts 11 in the form of a linear row. If one of the grooves or shafts 11, during the rotation of the separating body 4, passes into the transfer area with respect to the support 102, the lamellar spring 32 is raised to such an extent by the stationary magnet 36a that the grooves or shafts 11 are freed at the bottom and an article G can slide out downwards. The spring 32 is supported on the cover 10. A dropping out of the articles G is prevented by a bypass means 13 arranged in stationary manner only in the area. The support curve 15 now allows the article G to slide in the groove 11 initially up to completely below the spring 32. During further rotation of the support 102 in the direction indicated by the arrow, as a result of the stationary arrangement of the magnet 36a, its action on the spring 32 is eliminated, so that the latter closes the groove or shaft 11 and consequently prevents a further sliding of further articles G. Simultaneously the curve 15 is lowered and consequently permits a further sliding of the separated article G until it comes to rest concentrically or centrally in front of the suction hole 104. During a further rotation in the direction 50 the suction hole 104 reaches the stationary suction channel 106, so that still in the vicinity of the bypass means 13 the article G is subject to suction action by the vacuum exerted by a pump in the suction channel 106 and is consequently secured in this exactly defined position.

As soon as the article G has been moved past the camera system 130, it is illuminated with diffuse light by the lighting device 135a and is inspected by the camera 134a for defects on its outwardly directed top surface. The article G is then conveyed on by the support 102 until it reaches the transfer point 105. At this point the article is suctioned by means of the vacuum exerted in the suction channel 108 through a corresponding suction hole 107 against the latter, the transfer being assisted in that the suction hole 104 leaves the area of the stationary suction channel 106, i.e. the suction action is eliminated and the suction hole 107 reaches the area of the stationary suction channel 108, so that the suction action is correspondingly produced in the direction of the support 103. The vacuum in the suction channel 108 is such that it overcomes any suction forces still present in the suction channel 106 and the gravity of the article G to be inspected, so that the article G is transferred from support 102 to support 103. The article G is then moved past the camera systems 131, 132 and 133 and is inspected by the camera system 131 on its bottom side opposite to the top side inspected by the camera system 130 and which is now outwardly directed on the support 103. The camera systems 132 and 133 preferably inspect by means of the mirrors 138a and 138b the circumferential faces of the articles G.

The video images of the article G produced by the camera systems 130–133 are then transmitted to the image processing unit, where they are evaluated according to per se known methods. Divergences from the geometrical shape, e.g. due to larger breaks, can be easily detected in this way. For detecting smaller surface defects there is generally a nominal-actual value comparison between produced and stored images. As the articles G to be inspected have notches or embossings and with this respect cannot be separated in a positionally accurate manner, here a nominal-actual value comparison would require a mathematical rotation of the video images produced. This in turn increases the calculating effort and expenditure, as well as the time required to a significant extent. Thus, in the apparatus according to the invention evaluation takes place by evaluating the gradient of the grey value change of adjacent image points. Production-caused irregularities of the surface, such as notches or embossings, have relatively shallow gradients and regular paths, whereas defects have "steep" gradients and/or irregular paths, so that in this way it is possible to achieve a reliable inspection in the millisecond range with a correspondingly good resolution.

After inspection has taken place through the camera systems 130–133 the article G passes into the delivery area 40, 41 and 42 where the article G is delivered to one of the channels 44, 46 and 49 in accordance with the inspection result. If e.g. the evaluation has revealed that at least one video image of the article G produced is defective, then the blast nozzle 48 is activated on passing the particular article G and the later is ejected into the continuation channel 46. The activation signal is maintained until no further faulty article passes the ejecting device 42. If no defect is detected, the blast nozzle 47 is activated on passing a satisfactory article G and the latter passes into the continuation channel 44. Here again the activation signal is maintained for as long as satisfactory articles pass the ejecting device 41. If individual articles G are not ejected due to faults in the ejecting devices 47 and 48, they automatically drop into the continuation channel 49, because in this area the suction action for the article G declines, because there the end of the suction channel 108 is reached. Articles G ejected in this way into the continuation channel 49 are looked upon as faulty. Thus, the invention provides a self-monitoring or validatable system.

All parts coming into contact with the articles to be inspected can be easily replaced if the apparatus is to be used for inspecting other articles.

We claim:

1. An apparatus for inspecting small articles comprising:

a first rotatable support having a first circumferential surface for holding the small articles;

a second rotatable support having a second circumferential surface with the first and second circumferential surfaces being opposed to each other and spaced apart at a closest separation which is greater than a thickness of the small articles and is a transfer point for transferring the small articles from the first circumferential surface to the second circumferential surface;

a vacuum source coupled to suction holes disposed at spaced apart locations on the first circumferential surface for holding the small articles at the spaced apart locations during rotation to the transfer point;

a vacuum source coupled to suction holes disposed at spaced apart locations on the second circumferential surface for holding the small articles at the spaced apart location during rotation from the transfer point; and a plurality of detector devices, one of the plurality of detector devices being offset radially outward from and facing the second circumferential surface of the second rotatable support for viewing of a top or bottom surface of the small articles and at least another of the plurality of detector devices being positioned for viewing at least one other surface of the small articles.

2. An apparatus in accordance with claim 1 wherein:

another of the detector devices is offset radially outward from and facing the first circumferential surface of the first rotatable support for viewing another one of the top and bottom surface of the small articles and first and second additional detector devices of the plurality of detector devices are positioned for respectively viewing first and second other surfaces of the small articles each including a different part of a circumference separating the top and bottom surfaces.

3. An apparatus in accordance with claim 1 further comprising:

a device for supplying the small articles to the first support.

4. An apparatus in accordance with claim 1 further comprising:

a first stationary channel which is connectable to the vacuum source and the suction holes of the first circumferential surface; and a second stationary channel which is connectable to the vacuum source and the vacuum holes of the second circumferential surface.

5. An apparatus in accordance with claim 2, wherein the detector devices each comprise:

a camera system having a casing, a lighting device and a video camera.

6. An apparatus in accordance with claim 5 further comprising:

at least one mirror, each mirror for reflecting an image of a different one of the first and second other surfaces to a different video camera.

7. An apparatus in accordance with claim 5 wherein:

each lighting device has a plurality of light emitting diodes for respectively emitting different wavelengths of light.

8. An apparatus in accordance with claim 7 wherein:

diodes of the plurality of diodes having an identical wavelength are selectively switched on and off.

9. An apparatus in accordance with claim 8 wherein:

diodes of the plurality of diodes having an identical wavelength are detachable from the camera system.

10. An apparatus in accordance with claim 1 wherein:

the first and second rotatable supports have a color which is different than a color of the small articles.

11. An apparatus in accordance with claim 5 further comprising:

air exit openings in each of the casings facing the suction holes of the first and second circumferential surfaces; and a source of filtered pressurized air is coupled to the casings for causing filtered air to be blown toward the suction holes.

12. An apparatus in accordance with claim 1 further comprising:

first and second meshed toothed disks, the first meshed toothed disk being attached to an axis of rotation of the first support and the second meshed toothed disk being attached to an axis of rotation of the second support to provide synchronous drive of the supports.

13. An apparatus in accordance with claim 1 further comprising:

ejection devices mounted proximate to the second support for ejecting the small articles from the second support into respectively satisfactory and unsatisfactory groupings.

14. An apparatus in accordance with claim 13 wherein:

the ejection devices each comprise an air blast nozzle.

15. An apparatus in accordance with claims 1 further comprising:

a separating device having a fixed downwardly tapered hopper for supporting the small articles, the hopper having a downwardly extending cylindrical attachment forming a rotating section connected to the first support and an annular gap greater than a thickness of the small article concentric with the first support through which the small articles pass downward.

16. An apparatus in accordance with claim 1 further comprising:

a bypass having a support curve to supply the articles to the suction holes of the first support.

17. A method for inspecting small articles comprising:

providing the small articles to spaced apart locations on a first circumferential surface of a first support to which the small articles are held;

transferring the small articles held on the first circumferential surface to spaced apart locations on a second circumferential between surface of a second support at a transfer point disposed between the first and second support surfaces;

inspecting a top surface of each of the small articles held to the first circumferential surface with a first detector device;

inspecting a bottom surface of each of small articles held to the second circumferential surface with a second detector device; and inspecting at least one additional surface of each of the small articles held to the second circumferential surface with at least one additional detector device.

18. A method in accordance with claim 17 wherein:

the small articles are held to the first and second supports by a vacuum applied to suction holes extending radially outward through the first and second supports and distributed around the first and second circumferential surfaces.

19. A method in accordance with claim 17 further comprising:

separating the articles prior to being held on the first circumferential surface.

20. A method in accordance with claim 17 further comprising:

connecting the suction holes to a stationary suction channel which is coupled to the vacuum.

21. A method in accordance with claim 17 wherein:

the first and second supports are driven synchronously but in opposite directions so that the top surface of each of the small articles faces outward when held on the first support and the bottom surface of each of the small articles faces outward when held on the second support and the small articles are held on the first and second circumferential surfaces by a vacuum applied to suction holes extending outward through the supports to the first and second circumferential surfaces.

22. A method in accordance with claim 17 further comprising:

illuminating the small articles during inspection of each of the small articles.

23. A method in accordance with claim 17 wherein:

the detection devices are video cameras; and signals produced by the video cameras are transmitted to an evaluation device which performs fault detection of the small articles.

24. A method in accordance with claim 17 wherein:

a first ejection device ejects defect free small articles from the second circumferential surface; and a second ejection device ejects faulty small articles from the second circumferential surface.

25. A method in accordance with claim 24 wherein:

any small articles remaining on the second circumferential surface after ejection by the first and second ejection devices are classified as faulty and ejected as faulty articles.

26. A method in accordance with claim 18 wherein:

after each revolution of the first and second supports, the suction holes are supplied with compressed air opposite to a direction of suction.

27. A method in accordance with claim 23 wherein:

fault detection is performed by determining if a change in gray value of adjacent pixels in a video image of the small articles produced by the video cameras is present.

* * * * *